US00PP23390P2

(12) United States Plant Patent
Uebelhart

(10) Patent No.: US PP23,390 P2
(45) Date of Patent: Feb. 12, 2013

(54) ***HELOIPSIS* PLANT NAMED 'SUMMER PINK'**

(50) Latin Name: ***Heliopsis helianthiodes* var. *scabra***
Varietal Denomination: Summer Pink

(75) Inventor: Georg G. Uebelhart, Schwarmstedt (DE)

(73) Assignee: Jelitto Staudensamen GmbH, Shwarmstedt (DE)

( * ) Notice: Subject to any disclaimer, the term of this patent is extended or adjusted under 35 U.S.C. 154(b) by 101 days.

(21) Appl. No.: 13/065,161

(22) Filed: Mar. 15, 2011

(51) Int. Cl.
*A01H 5/00* (2006.01)

(52) U.S. Cl. ..... Plt./437

(58) Field of Classification Search ..... Plt./437
See application file for complete search history.

(56) References Cited

OTHER PUBLICATIONS

Darwin Plants—Perennials 2012. Retrieved on Aug. 2, 2012. Retrieved from the Internet at <www.darwinplants.com/site/genus.asp?GenusId=Heliopsis> 2 pp.*

* cited by examiner

*Primary Examiner* — June Hwu
(74) *Attorney, Agent, or Firm* — Penny J. Aguirre

(57) ABSTRACT

A new cultivar of *Heliopsis*, 'Summer Pink', characterized by its inflorescences with yellow and orange ray florets with red cones, its slightly curled foliage that is variegated with blades that are pink, green and creamy white in color with dark green veins, its stems that are dark reddish in color, and its ability to bloom predictably as a one-year-old plant.

2 Drawing Sheets

Botanical classification: *Heliopsis helianthoides* var. *scabra.*

Variety denomination: 'Summer Pink'.

CROSS REFERENCE TO A RELATED APPLICATION

This application is co-pending with a U.S. Plant Patent Applications filed for plants derived from the same cross in the Inventor's breeding program that are entitled *Heliopsis* Plant Named 'Summer Green' (U.S. Plant patent application Ser. No. 13/065,162) and *Heliopsis* Plant Named 'Summer Stripe' (U.S. Plant patent application Ser. No. 13/065,117).

BACKGROUND OF THE INVENTION

The present invention relates to a new and distinct cultivar of *Heliopsis* plant, botanically known as *Heliopsis helianthoides* var. *scabra* 'Summer Pink' and will be referred to hereinafter by its cultivar name, 'Summer Pink'.

'Summer Pink' was derived from a controlled breeding program conducted by the Inventor in a nursery in Schwarmstedt, Germany. The breeding program focuses on obtaining new cultivars of *Heliopsis* with novel leaf, stem, and flower colors and superior garden performance. 'Summer Pink' was selected in 2007 by the Inventor as a single unique plant derived in 2005 from a cross made between unnamed plants from his breeding program with the female parent identified with accession No. H04011 and the male parent identified with accession No. GU03.

Asexual reproduction of the new cultivar was first accomplished via stem cuttings under the direction of the Inventor in Lisse, the Netherlands in summer of 2008. Propagation by stem cutting and tissue culture has determined that the characteristics of this cultivar are stable and are reproduced true to type in successive generations.

SUMMARY OF THE INVENTION

The following traits have been repeatedly observed and are determined to be the characteristics of the new cultivar of *Heliopsis*. These attributes in combination distinguish 'Summer Pink' as unique from and all other varieties of *Heliopsis* known to the Inventor.

1. 'Summer Pink' exhibits inflorescences with ray florets that are yellow and orange at the base in color with red cones.
2. 'Summer Pink' exhibits slightly curled foliage that is variegated with blades that are pink, green and creamy white in color with dark green veins.
3. 'Summer Pink' exhibits stems that are dark reddish in color.
4. 'Summer Pink' blooms predictably as a one-year-old plant.

'Summer Pink' can be compared to its parents. The female parent is similar to 'Summer Green' in having reddish stems but differs from 'Summer Green' in having purplish green foliage without variegation. The male parent is similar to 'Summer Pink' in having variegated foliage but differs from 'Summer Green' in lacking red stems. 'Summer Pink' can also be compared to *Heliopsis* cultivar 'Loraine Sunshine' (U.S. Plant Pat. No. 10,690). 'Loraine Sunshine' is similar to 'Summer Pink' in having variegated foliage but differs from 'Summer Pink' in having green stems, inflorescences with a yellow cone, and in being less predictable in flowering as a one year-old plant. 'Summer Pink' can also be compared to cultivars from the same cross; 'Summer Stripe' and 'Summer Green'. 'Summer Stripe' differs from 'Summer Pink' in having yellow ray florets that lack an orange coloration at the base. 'Summer Green' differs from 'Summer Pink' in having variegated foliage that is creamy white with green veins and lacks any pink coloration in the foliage.

BRIEF DESCRIPTION OF THE DRAWINGS

The accompanying colored photographs illustrate the overall appearance and distinct characteristics of the new *Heliopsis*. The photographs were taken of a one year-old plant as grown in a 3.5-liter container in a cold-story greenhouse in Lisse, the Netherlands.

The photograph in FIG. 1 provides a side view of a plant of 'Summer Pink'.

Figure 1:
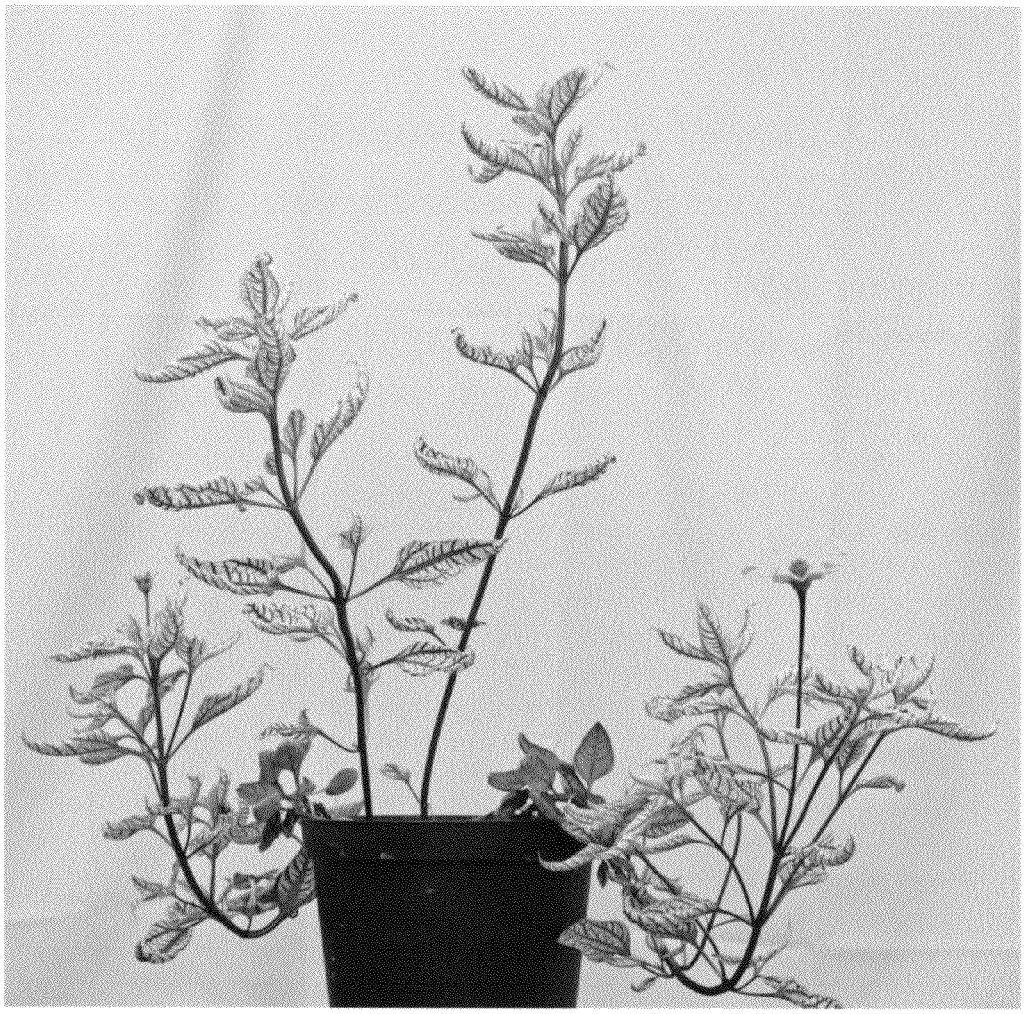
Figure 2:
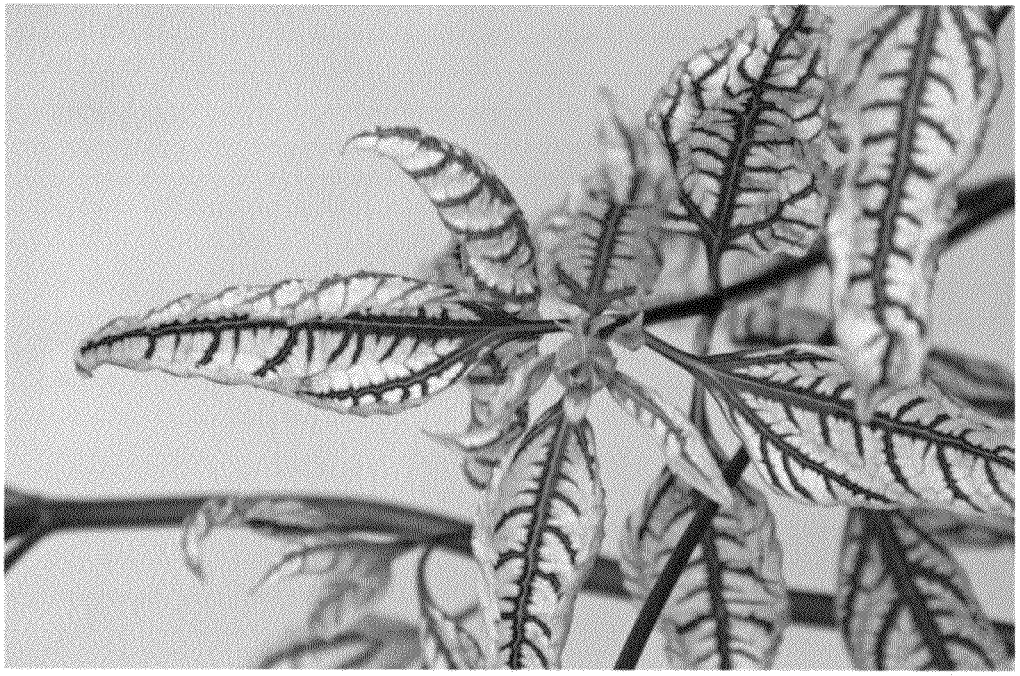

The photograph in FIG. 2 provides a close-up view of leaves of 'Summer Pink'.

Figure 3:
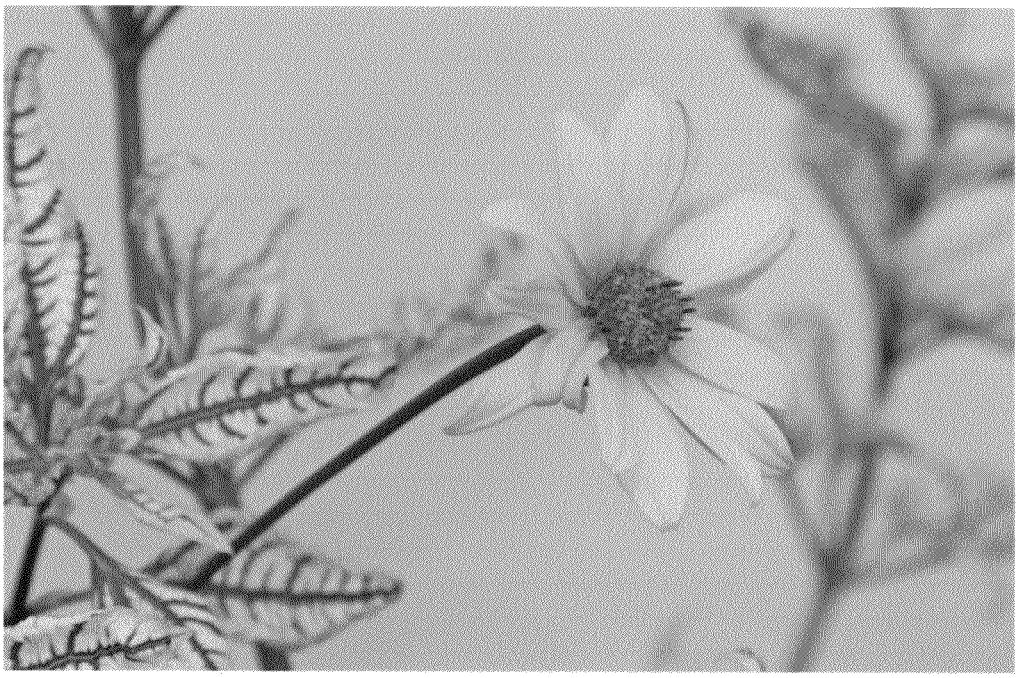

The photograph in FIG. 3 provides a close-up view of an inflorescence of 'Summer Pink'. The colors in the photographs are as close as possible with the digital photography and printing techniques utilized and the color codes in the detailed botanical description more accurately describe the colors of the new *Heliopsis*.

DETAILED BOTANICAL DESCRIPTION

The following is a detailed description of the new cultivar collected on one year-old plants grown in 3.5 liter containers in cold-storey greenhouses in Lisse, The Netherlands in June with day temperatures ranging between 18 to 30° C. and night temperatures ranging between 8 and 18° C. The phenotype of the new cultivar may vary with variations in environmental, climatic, and cultural, conditions, as it has not been tested under all possible environmental conditions. The color determination is in accordance with The 2007 R.H.S. Colour Chart of The Royal Horticultural Society, London, England, except where general color terms of ordinary dictionary significance are used.

General description:

*Blooming season*.—July to September in Germany.

*Plant habit*.—Herbaceous perennial, upright, clumping growth habit.

*Height and spread*.—About 120 cm in height and 60 cm in spread after 2 years.

*Hardiness*.—U.S.D.A. Zones 3 to 9.

*Diseases resistance*.—No susceptibility or resistance to diseases has been observed.

*Stress resistance*.—Moderate resistance to rain, high resistance to wind.

*Root description*.—Fibrous.

Growth and propagation:

*Propagation*.—Stem cuttings and tissue culture.

*Time from cutting to flowering*.—Average of 20 weeks.

*Crop maintenance*.—No pinching or pruning required.

*Growth rate*.—Vigorous, but slower growing in comparison to cultivars with green foliage.

Stem description:

*Stem shape*.—Rounded.

*Stem aspect*.—Average 30° from vertical.

*Stem strength*.—Moderate.

*Stem color*.—A blend of 177A, 200B and 200C.

*Stem surface*.—Young stems slightly pubescent, hairs 1 mm in length, 157D in color, deciduous, mature stems glossy, and glabrous.

*Lateral branch length*.—Average of 11.1 cm.

*Lateral branch diameter*.—Average of 2.5 mm.

*Quantity of lateral branches*.—About 24 per plant.

*Internode length*.—Average of 6.1 cm.

*Branching*.—Moderately branched.

Foliage description:

*Leaf division*.—Simple.

*Leaf shape*.—Ovate-lanceolate, strongly concave.

*Leaf base*.—Attenuate.

*Leaf apex*.—Acute.

*Leaf margin*.—Serrate.

*Leaf venation*.—Pinnate, upper surface 152A, lower surface 148A suffused with 177B.

*Leaf attachment*.—Petiolate.

*Leaf arrangement*.—Opposite.

*Leaf surface*.—Dull, upper and lower surfaces moderately strigose with strigose hairs 0.5 mm in length and 157D in color.

*Leaf color*.—Young foliage upper surface; a blend of 150D and 154D with pinnate veins 152A and reticulate veins a blend of 144A and 144B, young foliage lower surface; 150D with pinnate veins 148A suffused with 177B and reticulate veins 144C, mature foliage upper surface; 158D with pinnate veins 152A and reticulate veins N137C, mature foliage lower surface; 158D suffused with 184C with pinnate veins 148A suffused with 177B and reticulate veins 138A.

*Leaf size*.—Average of 6.5 cm in length and 3.3 cm in width.

*Petiole*.—Smooth, 2.4 cm in length and 1.5 mm in diameter, upper surface; moderately glossy and 148A in color, lower surface; very glossy and 148A in color and suffused with 177B.

Flower description:

General description:

*Inflorescence type*.—Terminal capitulum with many disc florets, one row of ray florets, and two rows of involucral bracts.

*Flowering response*.—9 weeks.

*Rate of flowering*.—Staggered starting from the terminal inflorescence towards the youngest lateral inflorescence.

*Lastingness of inflorescence*.—About 6 weeks, persistent.

*Fragrance*.—Faint chrysanthemum-like.

*Quantity of inflorescences*.—1 per lateral stem, 28 per plant.

*Inflorescence buds*.—About 1.2 cm in depth and 1.7 cm in diameter, flattened globular in shape, a blend of 144A and 144B in color.

*Inflorescence size*.—About 2.1 cm in depth and 6.1 cm in diameter, diameter of disk about 1.4 cm, height of disk about 1.9 cm.

*Receptacle*.—Triangular, about 6 mm in depth and 3 mm in diameter, 155C in color.

*Peduncle*.—Round with axial ribs, moderately strong, a blend of 148A and 152A suffused with 177A, about 11.9 cm in length, 2 mm in diameter, surface is slightly pubescent.

*Involucral bracts (phyllaries)*.—Oblong in shape, 18 per inflorescence, arranged in 2 rows, broadly acute apex, broadly cuneate base, margin entire, 157D in color, upper surface 143B, lower surface a blend of 143B and 143C, about 9 mm in length, 3 mm in width, surface dull and moderately strigose with hairs about 1 mm in length on upper and lower surface.

Ray florets (capitulate):

*Number*.—Average of 14.

*Arrangement*.—Rotate.

*Appearance*.—Smooth, dull.

*Shape*.—Elliptic.

*Aspect*.—Slightly upright at an angle of 10° from horizontal.

*Size*.—Average of 3.3 cm in length and 1 cm in width.

*Petal apex*.—Praemorse.

*Petal base*.—Cuneate.

*Petal margins*.—Entire.

*Petal texture*.—Smooth, slightly ribbed lengthwise.

*Petal color*.—Opening; upper surface 14A with base 23A and lower surface 13A, fully open; upper surface 14A and lower surface a blend of 13A and 13B, color not fading.

Disk florets (perfect):

*Quantity*.—Average of 100.

*Shape*.—Tubular, sympetalous with 5 lobes comprising upper 12.5% of floret.

*Arrangement*.—Spiral concentric towards center of disc.

*Disk lobe apex*.—Acute.

*Disk lobe margin*.—Entire.

*Petal base*.—Fused.

*Petal texture*.—Smooth, dull on inner and outer surface.

*Size*.—About 1.1 cm in length and 2.5 mm in width.

*Color*.—Bud; base 145C, mid-section and apex 152D, opening; base 145D, mid-section 152D, apex 24A, fully opened; base 145D, mid-section 152D, apex 53A.

Reproductive organs:

*Presence*.—Disk flowers are perfect, ray flowers are carpellate.

*Gynoecium*.—1 pistil per disk and ray floret, 1.2 cm in length, stigma decurrent and 28A in color, style 9 mm in length and a blend of 151C and 151D in color, ovary 145D in color.

*Androecium*.—5 stamen per disk floret, filament 2 mm in length and 157D in color, anther linear in shape, 3 mm in length and 152A in color, pollen moderate to abundant in quantity and 17B in color.

*Fruit and seed*.—No fruits or seeds observed to date.

It is claimed:

1. A new and distinct cultivar of *Heliopsis* plant named 'Summer Pink' as herein illustrated and described.

* * * * *

UNITED STATES PATENT AND TRADEMARK OFFICE

CERTIFICATE OF CORRECTION

PATENT NO. : PP23,390 P2
APPLICATION NO. : 13/065161
DATED : February 12, 2013
INVENTOR(S) : Georg G. Uebelhart It is certified that error appears in the above-identified patent and that said Letters Patent is hereby corrected as shown below:

On the title page item (54) "HELOIPSIS PLANT NAMED 'SUMMER PINK'" SHOULD READ

-- HELIOPSIS PLANT NAMED 'SUMMER PINK' --

Signed and Sealed this
Ninth Day of April, 2013

Teresa Stanek Rea
*Acting Director of the United States Patent and Trademark Office*